United States Patent [19]

Mersan

[11] 3,970,085
[45] July 20, 1976

[54] OSTOMY APPLIANCES AND SEALING ELEMENTS

[75] Inventor: Elayne R. Mersan, Minocqua, Wis.

[73] Assignee: Marsan Manufacturing Company, Inc., Wausau, Wis.

[22] Filed: Nov. 29, 1974

[21] Appl. No.: 528,348

[52] U.S. Cl. ............................................. 128/283
[51] Int. Cl.² ......................................... A61F 5/44
[58] Field of Search ..................... 128/283, DIG. 24

[56] References Cited
UNITED STATES PATENTS

| 3,040,745 | 6/1962 | Tezak | 128/283 |
| 3,077,192 | 2/1963 | Berger | 128/283 |
| 3,283,757 | 11/1966 | Nelsen | 128/283 |
| 3,481,336 | 12/1969 | Ipson | 128/283 |
| 3,690,320 | 9/1972 | Riely | 128/283 |
| 3,773,048 | 11/1973 | Kirkliauskas | 128/283 |
| 3,826,262 | 7/1974 | Blackwood | 128/283 |

FOREIGN PATENTS OR APPLICATIONS

| 1,105,558 | 4/1961 | Germany | 128/283 |

*Primary Examiner*—John D. Yasko
*Attorney, Agent, or Firm*—Merriam, Marshall, Shapiro & Klose

[57] ABSTRACT

Disclosed are appliances for post-surgical collection of discharges from the stoma of an ostomy patient, which appliances include sealing elements in the form of a soft, pliable tubularly flanged washer element and a tubularly flanged base gasket having a groove element for securing the washer.

10 Claims, 5 Drawing Figures

OSTOMY APPLIANCES AND SEALING ELEMENTS

BACKGROUND

The present invention relates generally to appliances for use in collection of discharges from the stoma of an ostomy patient and more particularly relates to improved apparatus for forming a comfortable, reliable seal between the ostomy site and the interior of a collection pouch or drain.

Apparatus presently employed in the collection of a waste material ordinarily includes a relatively rigid, apertured base gasket which is supported on the abdominal wall of the patient by means of belts, adhesives and the like. Ordinarily such base gaskets include a centrally-disposed tubular flange designed to extend through an opening in the operative back wall of a disposable collection pouch which is adhered to the surface of the gasket. In operation, such gasket and pouch assemblies are mounted on the patient with the stoma protruding through the base gasket tubular flange in the direction of the pouch. The sensitive tissue of and around the stoma is protected from excoriation by the wastes through the use of a soft, pliable annular washer of karaya gum or other similar material. Such a washer is ordinarily disposed around the stoma between the base gasket and the wearer's abdomen.

The basic problem in the use of such a combination is the tendency for body heat to melt the washer element. The resultant oozing of washer material outwardly from the base gasket will soil the clothing and bed clothing of the patient. Another problem with such a combination results from the general bulkiness of the washer when disposed between the base gasket and the patient's abdomen. As a rule, longer lasting washers are thicker and thus make more difficult a close fit of the ordinarily rigid base gasket against the abdomen.

BRIEF DESCRIPTION

According to the present invention there is provided an improved collection appliance including sealing systems incorporating a base gasket having a central tubular flange, which flange has a radially outwardly-extending front wall provided with an annular depression. Also incorporated is a soft pliable washer element in the form of a stoma-accommodating flattened annular ring having a tubular flange member. The flange member is registerable within the gasket tubular flange and the ring pliably sealable in place through accommodation of a portion of the ring in the depression of the gasket flange front wall.

Also provided according to the invention are composite collection appliances including base gasket and washer elements as above-described together with pouch or drain elements and means for mounting the entire appliances together and in an operative position.

Other aspects and advantages of the present invention will be understood from the following detailed description of presently preferred embodiments, considered in connection with drawings wherein.

DETAILED DESCRIPTION

Figure 1:
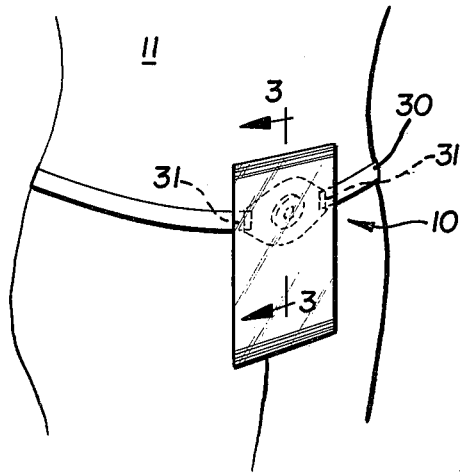
FIG. 1 is a front elevation of an assembly according to the disclosure of the invention in position on a wearer.
Figure 2:
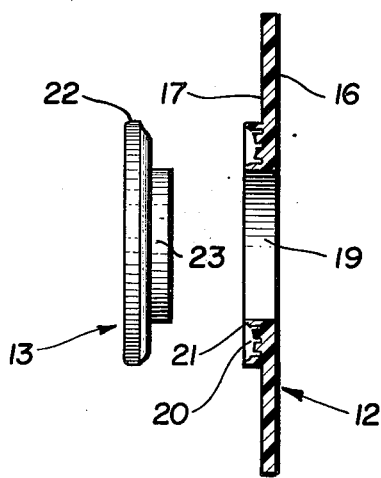
FIG. 2 is an exploded sectional view of a washer and base gasket element assembly of the invention.
Figure 4:
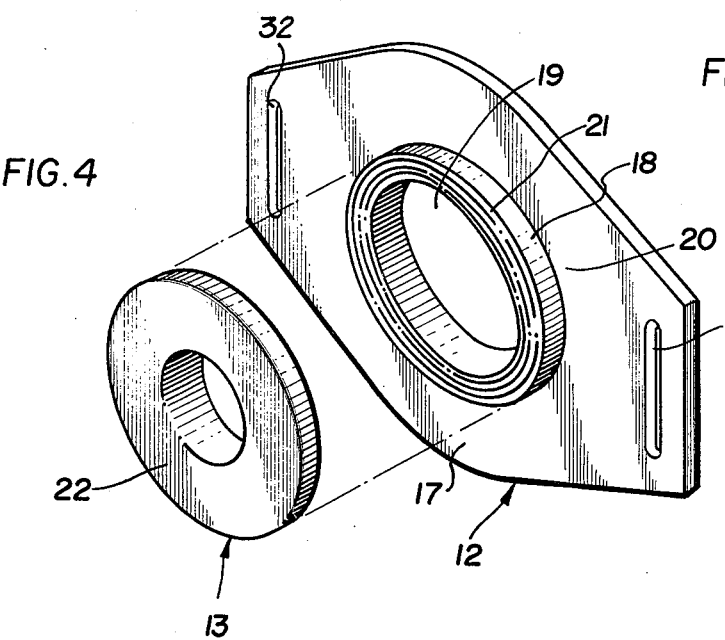
FIG. 4 is an exploded perspective view of a gasket and washer element as in FIG. 2.
Figure 3:
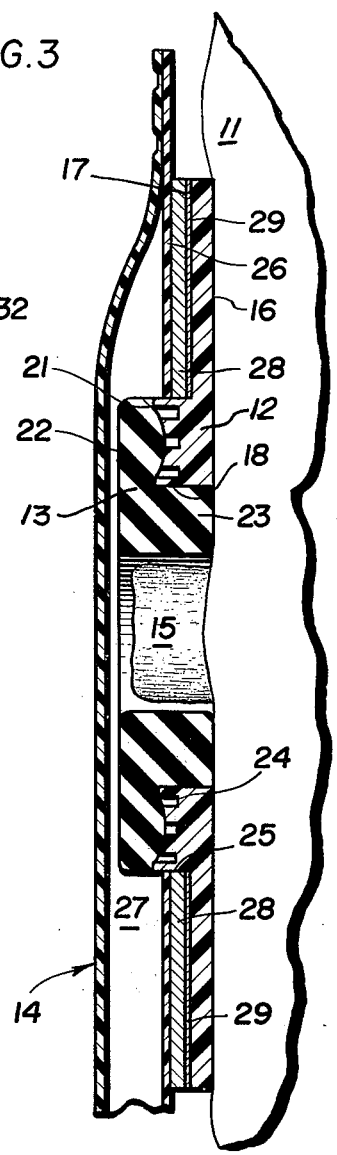
FIG. 3 is a sectional view of an appliance according to the invention, shown operatively mounted in place.

Illustrated in FIG. 1 is appliance 10 according to the present invention shown secured to the abdominal wall 11 of an ostomy patient. Mounting of the appliance 10 is illustrated in greater detail in FIG. 3 wherein the appliance is seen to include a base gasket 12, a pliable washer element 13 and a pouch or drain element 14 on the abdominal wall 11, about the stoma 15 of the patient.

Base gasket 12 is preferably fabricated of relatively rigid plastic material formed to provide an operative back surface 16 which in use abuts the abdominal wall 11 of the patient in the area surrounding the stoma 15. Extending from the operative front surface 17 of gasket 12 is a tubular flange 18, annularly disposed about gasket central aperture 19. At least one depression 20 is formed in the radially outwardly-extending front wall 21 of flange 18 and preferably is an annular depression as illustrated.

Base gasket 12 is ordinarily secured to abdominal wall 11 by means of surgical adhesions or an elastic belt 30 with fasteners 31, 31.

Washer element 13 has a form similar to that disclosed in U.S. Pat. No. 3,520,301, and as such has flattened annular ring portion 22 and a stoma-accommodating, generally tubular flange portion 23 which is dimensioned to allow its registry within aperture 19 of flange 18. Ring portion 22 is positioned and dimensioned so that, when tubular portion 23 is registered in aperture 19, at least a portion of ring 22 will pliably engage in depression 20 in gasket flange front wall 21.

Washer element 13 may be manufactured of any suitable gel-like material, such as a mixture of karaya gum and glycerol, to provide sufficient softness in areas of contact with the stoma 15 as well as sufficient pliability at ambient temperatures to allow firm engagement of a portion of ring 22 in depression 20.

Secure pliable engagement of a portion of ring 22 in depression 20 may be facilitated through the use of a bead or coating of adhesive material 24, applied either on ring 22 or in depression 20 or both.

Pouch or drain element 14 may be of standard plastic film construction and includes a stoma-accommodating opening 25 in its operative back wall 26. Opening 25 is preferably dimensioned to allow registry of flange 18 therethrough and consequently to provide direct access for the stoma to the interior 27 of bag 14. In the preferred embodiment of FIG. 3, and apertured gasket element 28 is sealed about opening 25 and, in operation, gasket 28 is sealingly secured to base gasket operative front surface 17 by an adhesive material 29. Alternatively, gasket 28 may be secured abutting base gasket front surface 17 by means of a belt 30 having fasteners 31 for releasably retaining gasket 28 superimposed on the base gasket. For such purpose gasket 28 would be provided with slots (not shown) laterally corresponding to slots 32 of base gasket 12.

Figure 5:
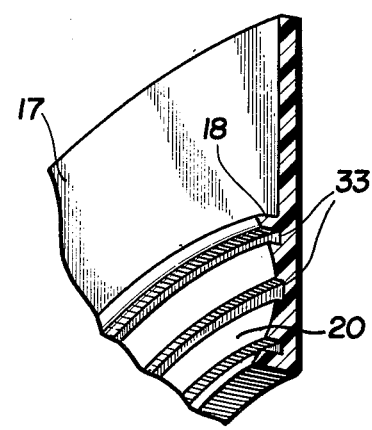
FIG. 5 is an enlarged fragmentary view of a gasket element flange front surface according to the invention.

FIG. 5 illustrates preferred embodiment base gasket tubular flange 18 wherein the surface area of depression 20 in wall 21 is increased through provision of one or more annular grooves 33.

Preferred embodiments of base gasket 12 may be fabricated with tubular flange 18 extending normally outwardly about 1/16 of an inch from gasket front surface 17, base gasket 12 itself having a thickness of about 1/16 of an inch. Flange front wall 21 preferably has transverse dimension of about ¼ of an inch. Tubular flange 23 of washer 13 should preferably have an outer diameter somewhat less than the inner diameter aperture 19 of gasket 12 to permit easy registry therein and ring 22 should preferably extend radially outwardly at least about ⅛ of an inch to allow for pliable engagement in depression 20.

Obviously, modifications and variations of the above-described invention may be made without departing from the spirit and scope thereof. Therefore, only such limitations as are indicated by the appended claims should be placed thereon.

What is claimed is:

1. In appliances for post-surgical collection of discharges from the stoma of a patient, an improvement is a combination of sealing elements, said improvement comprising:
   a base gasket element having an operative front surface and a flat back surface and including,
   a centrally disposed aperture,
   a tubular flange annularly disposed about said aperture and extending outwardly substantially normally from said gasket front surface, said tubular flange having a radially outwardly extending front wall,
   at least one depression in said tubular flange front wall; and
   a pliable washer element, said washer element including,
   a radially outwardly-extending annular ring element, and,
   a centrally-disposed stoma-accommodating tubular flange extending outwardly substantially normally from said ring element and having a substantially flat face adapted to contact with and seal against the skin of a patient around the stoma,
   said washer element ring and flange being so dimensioned that said washer flange is registerable within said gasket flange and at least a portion of said washer ring is pliably engageable within said annular depression of said gasket tubular flange front wall when said washer flange is registered within said gasket tubular flange.

2. Apparatus as set forth in claim 1 wherein said depression in said tubular flange front wall is an annular depression.

3. Apparatus as set forth in claim 2 further including at least one annular groove in said annular depression in said flange front wall.

4. Apparatus as set forth in claim 1 further including means for mounting said gasket in an operative position with said gasket operative back surface adjacent the obdomen of a patient and the stoma of the patient passing through said gasket aperture.

5. Apparatus as set forth in claim 4 wherein said mounting means includes a pair of laterally opposed slotted flanges on said gasket.

6. Apparatus as set forth in claim 1 further including adhesive means for facilitating engagement of said washer ring in said depression.

7. Apparatus for post-surgical collection of discharges from the stoma of a patient, said apparatus comprising:
   a base gasket element having operative front and back surfaces and including,
   a centrally disposed aperture,
   a tubular flange annularly disposed about said aperture and extending outwardly substantially normally from said gasket front surface, said tubular flange having a radially outwardly-extending front wall,
   at least one depression in said tubular flange front wall with an outer peripheral edge;
   a pliable washer element, said washer element including,
   a radially outwardly-extending annular ring element with an outer peripheral edge which substantially coincides with the tubular flange outer peripheral edge, and,
   a centrally-disposed stoma-accommodating tubular flange extending outwardly substantially normally from said ring element and having a substantially flat face adapted to contact with and seal against the skin of a patient around the stoma,
   said washer element ring and flange being so dimensioned that said washer flange is registerable within said gasket flange and at least a portion of said washer ring is pliably engageable within said annular depression of said gasket tubular flange front wall when said washer flange is registered within said gasket tubular flange;
   a waste material collection pouch having a stoma-accommodating opening therein;
   means for mounting said pouch in operative position with said gasket tubular flange registered through said pouch opening; and
   means for mounting said gasket in operative position with the stoma of a patient registered through said gasket central aperture.

8. Apparatus as set forth in claim 7 wherein said mounting means includes a retainer gasket element the operative front surface of which is affixed to said pouch about said pouch opening and the operative back surface of which is coated with an adhesive material.

9. In appliances for post-surgical collection of discharges from the stoma of a patient, an improvement in a combination of sealing elements, said improvement comprising:
   a base gasket element having an operative front surface and a flat back surface and including,
   a centrally disposed aperture,
   a tubular flange annularly disposed about said aperture and extending outwardly substantially normally from said gasket front surface, said tubular flange having a radially outwardly-extending front wall with an outer peripheral edge,
   at least one depression in said tubular flange front wall; and
   a pliable washer element, said washer element including,
   a radially outwardly-extending annular ring element with an outer peripheral edge which substantially coincides with the tubular flange outer peripheral edge, and,
   a centrally-disposed stoma-accommodating tubular flange extending outwardly substantially normally from said ring element and having a substantially flat face adapted to contact with and seal against the skin of a patient around the stoma,
   said washer element ring and flange being so dimensioned that said washer flange is registerable within said gasket flange and at least a portion of said washer ring is pliably engageable within said annular depression of said gasket tubular flange front wall when said washer flange is registered within said gasket tubular flange.

10. Apparatus as set forth in claim 1 in which: the washer ring has a rear surface adapted for sealing contact with substantially the entire surface of the radially outwardly extending front wall of the tubular flange.

* * * * *

UNITED STATES PATENT AND TRADEMARK OFFICE
CERTIFICATE OF CORRECTION

PATENT NO. : 3,970,085
DATED : July 20, 1976
INVENTOR(S) : Elayne R. Marsan

It is certified that error appears in the above-identified patent and that said Letters Patent are hereby corrected as shown below:

Title page, Inventor's name should be --Marsan-- not "Mersan";
Column 3, line 20, "is" should be --in--;
Column 3, line 58, "obdomen" should be --abdomen--.

Signed and Sealed this

Nineteenth Day of October 1976

[SEAL]

Attest:

RUTH C. MASON
Attesting Officer

C. MARSHALL DANN
Commissioner of Patents and Trademarks